(12) United States Patent
Weill et al.

(10) Patent No.: US 8,642,100 B2
(45) Date of Patent: Feb. 4, 2014

(54) METHOD TO EVALUATE THE QUANTITY OF METHANE PRODUCED BY A DAIRY RUMINANT AND METHOD TO REDUCE AND CONTROL THIS QUANTITY

(75) Inventors: Pierre Weill, Vern sur Seiche (FR); Guillaume Chesneau, Luitre (FR); Yves Chilliard, Ceyrat (FR); Michel Doreau, Saint Saturnin (FR); Cécile Martin, Saint Saturnin (FR)

(73) Assignee: Valorex (FR)

( * ) Notice: Subject to any disclaimer, the term of this patent is extended or adjusted under 35 U.S.C. 154(b) by 684 days.

(21) Appl. No.: 12/452,243

(22) PCT Filed: Jun. 24, 2009

(86) PCT No.: PCT/EP2009/057919
§ 371 (c)(1),
(2), (4) Date: Dec. 18, 2009

(87) PCT Pub. No.: WO2009/156453
PCT Pub. Date: Dec. 30, 2009

(65) Prior Publication Data
US 2011/0081442 A1  Apr. 7, 2011

(30) Foreign Application Priority Data

Jun. 25, 2008  (FR) ...................................... 08 54230

(51) Int. Cl.
*A23K 1/18*   (2006.01)
*G01N 33/00*  (2006.01)
*G01N 7/00*   (2006.01)

(52) U.S. Cl.
USPC ................................... 426/2; 73/866; 73/23.2

(58) Field of Classification Search
USPC ........ 426/551, 623, 635, 636, 658, 2; 73/866, 73/23.2
See application file for complete search history.

(56) References Cited

FOREIGN PATENT DOCUMENTS

WO  WO-2006040537 A1   4/2006
WO  WO-2007141416 A1  12/2007

OTHER PUBLICATIONS

Dong et al, Lipid-induced depression of methane production and digestibility in the artificial rumen system (RUSITEC). 1997. Can. J. Anim. Sci. 77:269-278.*
Johnson et. al., The Effect of Oilseeds in Diets of Lactating Cows on Milk Production and Methane Emissions. 2002. J. Dairy Sci. 85:1509-1515.*

(Continued)

*Primary Examiner* — Rena Dye
*Assistant Examiner* — Lela S Williams
(74) *Attorney, Agent, or Firm* — Lerner, David, Littenberg, Krumholz & Mentlik, LLP

(57) ABSTRACT

The present invention relates in particular to a method to evaluate the quantity of methane produced by a dairy ruminant.
It is notably characterized by the fact that it comprises determination of the ratio between the quantity of fatty acids with 16 carbon atoms or less, called FA<C16 and the sum of the total fatty acids of the milk, said fatty acids being found in the milk produced by said ruminant, said quantity of methane being defined by the following equation:

Quantity $CH_4 = (FA<C16/\text{Total FAs})^a * (\text{milk production})^b$ in which:
quantity $CH_4$ (in g/liter of milk)=quantity of methane produced;
FA<C16=quantity of fatty acids with 16 carbon atoms or less;
Total FAs=total quantity of fatty acids;
expression of the ratio (FA<C16)/(Total FAs) as a % of total FAs;
milk production=quantity of milk produced in kg of milk/animal and per year;
a and b are numerical parameters in which a lies between 10 and 13, and b lies between −0.40 and −0.45.

6 Claims, 1 Drawing Sheet

(56) References Cited

OTHER PUBLICATIONS

Ellis J. et al.: "prediction of methane production from dairy and beef cattle" Journal of Dairy Science, 2007, pp. 3456-3467, XP002509496.

Soyeurt H et al: "Estimating *fatty* acid content in cow milk using mid-infrared pectrometry" Journal of Dairy Science, American Dairy Science Association, Savoy, IL, US, vol. 89, No. 9, (Sep. 1, 2006), pp. 3690-3695, XP02455357.

International Search Report, PCT/EP2009/057919, dated Oct. 7, 2009.

Martin et al., Journal of Animal Science, 1-25, (May 2008).

Gworgwor et al., Journal of Sustainable Development in Agriculture and Environment, 2. 2(1); 1-14, (2006).

Vlaeminck et al., Comm. Appl. Biol. Sci., 70(2); 43-46 (2005).

Leseur et al., "The Carbon markets : which place for French agriculture?", 1-118 (2006).

* cited by examiner

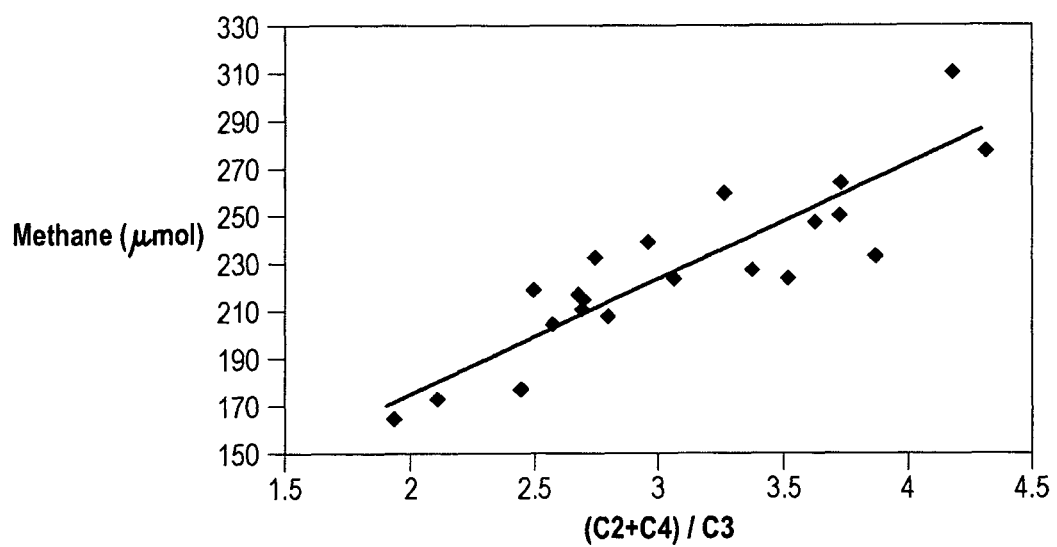

METHOD TO EVALUATE THE QUANTITY OF METHANE PRODUCED BY A DAIRY RUMINANT AND METHOD TO REDUCE AND CONTROL THIS QUANTITY

CROSS REFERENCE TO RELATED APPLICATIONS

The present application is a national phase entry under 35 U.S.C. §371 of International Application No. PCT/EP2009/057919, filed Jun. 24, 2009, which claims benefit of French Application No. 08 54230 filed Jun. 25, 2008. The disclosures of all of said applications are incorporated by reference herein.

The present invention lies in the area of animal feed, and more precisely in the area of feed for milk-producing animals.

It more particularly concerns a method to evaluate the quantity of methane produced by a dairy ruminant, and a method to control the quantity of methane produced by a dairy ruminant.

The digestion of organic matter by ruminants comprises a microbial fermentation phase in the rumen. During this phase, plant polysaccharides (such as cellulose, hemicellulose, pectin, and starch) are broken down by the anaerobic bacteria living in the rumen.

This gives rise to the production of various volatile fatty acids (VFAs) (acetate, propionate, and butyrate [in increasing order of importance], carbon dioxide [$CO_2$] and hydrogen [$H_2$]).

Since the rumen is an anaerobic medium, the production of energy (ATP) occurs by "hydrogen transfer".

Hydrogen inhibits the activity of most bacteria via different mechanisms. The hydrogen produced must therefore be eliminated by the rumen to promote good microbial digestion.

Methanogenesis, leading to the formation of methane ($CH_4$), is the main route allowing this elimination. It can be symbolized by the following reaction:

$$[CO_2 + 4H_2] = CH_4 + 2H_2O$$

This conversion is ensured by methanogenic bacteria which live in association with protozoa (which form the rumen's microfauna).

Methane ($CH_4$), together with carbon dioxide ($CO_2$), nitrous oxide ($N_2O$), and the three halogen carbons (Chlorofluorocarbons CFCs, hydrofluorocarbons HFCs, and perfluorocarbons PFCs), is one of the main greenhouse gases (GGs).

Its contribution to the greenhouse effect is very considerable. One molecule of $CH_4$ is effectively equivalent to 21 molecules of $CO_2$, according to official equivalence tables.

These GGs are believed to have an effect on climate change and in particular on global warming. Since the World Earth Summit in Rio in 1992, the fight against these changes has become an international commitment which, in 1997, translated as quantitative commitments taken under the Kyoto protocol.

The European Council has set itself the target of reducing GGs by 20% between now and 2020. In 2003, livestock farming generated 47.7 MMTCDE (million metric tons of carbon dioxide equivalent) of which 28.3 MMTCDE in the form of methane derived from the digestive fermentation of ruminants (Leseur, 2006; Martin et al., 2006).

These methane emissions represent 26% of emissions by the farming sector and 5% of French GG emissions (Leseur, 2006).

It therefore appears necessary to reduce the methane emissions of ruminants.

Different solutions have been put forward to reach this objective.

The first consists of limiting the consumption of products derived from ruminants and in particular dairy products, the effect of which would be to reduce the number of these dairy ruminants and hence logically the emissions of methane.

However, dairy products have been present in the food of human beings since time began. Man is known to be the only animal species to eat dairy products after weaning. Also, at nutritional level, these dairy products contain calcium, proteins, and lipids with very special nutritional properties which cannot be dissociated from a balanced diet at all stages of life.

Additionally, the increase in the planet's population appears scarcely compatible with a reduction in numbers of livestock intended to feed this increasing population.

Another solution consists of changing the feed of dairy ruminants (cows, sheep, goats, etc.) by directing the mechanisms of rumination towards decreased methane production.

Different techniques have been suggested to reach this objective.

The first consists of increasing the quantity of milk produced per cow (intensified livestock farming).

The second provides for additives in the feed that are toxic for protozoa and/or methanogenic bacteria so that milk can be produced with a reduction in the emitted quantities of methane.

Finally, a third technique consists of adding sources of plant lipids high in unsaturated fatty acids to the feed of dairy ruminants, preferably from the Omega-3 family, or in the form of other unsaturated fatty acids although their effects on methanogenesis are less powerful (than those of Omega-3 fatty acids). These fatty acids are toxic for methanogenic bacteria, either directly or via the toxic effects on protozoa which live in association with these methanogenic bacteria.

However, these different techniques can only be of real interest if there is a practical method, that is easy to implement, to evaluate the quantity of methane produced by ruminants.

Yet, measurement of methane emissions at the present time is only possible at experimental stations, but in cumbersome costly manner.

The present invention sets out to overcome this shortcoming.

Therefore, according to a first aspect, the present invention concerns a method to evaluate the quantity of methane produced by a dairy ruminant, characterized by the fact that it comprises determination of the ratio between the quantity of fatty acids with 16 carbon atoms or less, called FA<C16, and the sum of the total fatty acids in the milk, said fatty acids being those present in the milk produced by said ruminant, said quantity of methane being defined by the following equation:

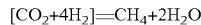

Quantity $CH_4 = (FA<C16/\text{total FAs})*a*(\text{milk production})^b$ in which:
quantity $CH_4$ (in g/liter of milk)=quantity of methane produced; FA<C16=quantity of fatty acids with 16 carbon atoms or less; Total FAs=total quantity of fatty acids; expression of the ratio (FA<C16)/(Total FAs) as a % of Total FAs; milk production=quantity of milk produced in kg milk/per animal/per year;
a and b are numerical parameters, with a lying between 10 and 13 and b lying between −0.40 and −0.45.

This method is easy to implement since the present applicant has evidenced that the quantity of methane produced is directly related to the quantity of fatty acids in the milk. Also, the assay of fatty acids in milk is an operation that is currently given very wide application and does not require any sophisticated or costly means. In one preferred embodiment, a and b are respectively 11.368 and −0.4274.

Another aspect of the invention relates to a method to reduce and control the quantity of methane produced by a dairy ruminant.

This method is noteworthy in that it consists of:
giving the ruminant a food ration which meets at least one of the following criteria:
a) it excludes all fat of animal origin;
b) it limits the exogenous intake of vegetable oil containing more than 30% Total FA in the form of saturated FAs, in the natural state, hydrogenated, or saponified, to no more than 15 grams/animal and per 100 kg live weight;
c) it contains at least one lipid source high in omega-3 alpha-linolenic acid (ALA), i.e. of which more than 30% of the Total FAs are in the form of omega-3 FAs;
and of controlling said quantity of methane by applying the method according to one of the preceding characteristics.

Preferably, this lipid source is in the form of grazed fodder or conserved forage (wilted grass, silage, wrapped round bale, dehydrated, etc.) or oil seeds (in the natural state, raw, or cooked) high in ALA and oil-cakes of these same oil seeds.

Advantageously, said source includes flax (linseed).

Other characteristics and advantages of the invention will become apparent from the following detailed description.

1—Production of Volatile Fatty Acids (VFAs) and Production of Methane ($CH_4$)

The link between the production of VFAs in the rumen and the production of methane has been known and researched for many years.

It has been shown for example that the production of acetate and butyrate releases hydrogen, and therefore promotes the production of methane, whereas the production of propionate allows the hydrogen to be used and hence limits methane production (Gworgwor et al., 2006).

This can be illustrated by the following equations:

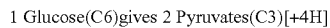

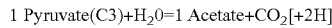

and:

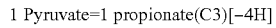

A predictive equation has therefore been developed to predict the production of $CH_4$ from the production of VFAs, using the graph given in appended FIG. 1 (Moss et al., 2000). Therefore, the greater the production of C2 and C4 by fermentations in the rumen, the greater the production of $CH_4$.

Conversely, the greater the production of C3 by fermentations in the rumen, the more the production of $CH_4$ is reduced.

The synthesis equation following therefrom is defined as follows: $[CH_4]=0.45$ [acetate]$+0.40$ [Butyrate]$-0.275$ [Propionate]
where [x]=quantity of x, as a % of Total VFAs.

2—Influence of the Intake of a Source (Digestible in the Rumen) of Omega-3 Alpha-Linolenic Acid (ALA) on the Production of VFAs and $CH_4$ Omega-3-alpha-linolenic acid or C18: 3 n−3 or "ALA" is one of the mass constituents of growing plants.

It is found in abundance for example in young grass and in algae in which it accounts for the vast majority (50 to 75%) of the fatty acids in these plants. ALA is a basic constituent of chlorophyll membranes.

ALA is also found in some oilseeds such as flax seed (45% to 70%), hemp (around 15%), rapeseed or soy (around 10%).

The ALA content in the ration of dairy ruminants modifies the microbial population present in the rumen. ALA, directly and indirectly, effectively inhibits methanogenic bacteria and significantly modifies the proportions of VFAs produced, in particular by lowering the quantities of acetate and butyrate produced.

According to numerous sources in the scientific literature, when an ALA source is added to the ration of a ruminant, the production of propionic acid (C3) increases, and the proportions of acetic acid (C2) and butyric acid (C4) are reduced.

It therefore appears that:
the ratio [(C2+C4) to C3] is a very good index for the production of methane in the rumen;
the intake of ALA in the diets of dairy ruminants has a linear effect on the ratio (C2+C4)/C3 which is regularly decreased when, all other things being equivalent, the quantity of ALA ingested by the ruminant is increased.

It is to be noted, however that ALA sources can have different effects depending on the site of ALA digestion.

For example, raw flax seeds only bring a scarce reduction in the ratio [(C2+C4)/C3)], whereas extruded flax seeds and flax seed oils bring a strong increase.

The ability to modify this ratio [(C2+C4)/C3)] is therefore related to the quantity of ALA in animal diet but also to the availability of ALA in the rumen.

3—Influence of the Ratio [(C2+C4)/C3)] on Milk Composition

VFAs (C2, C3, or C4) produced by the rumen are diffused through its walls, or move on further through the intestinal barrier to enter circulating fluids.

Propionic acid (C3) is used as "glucogenic" source and contributes towards milk production as lactose precursor.

On the contrary, acetic (C2) and butyric (C4) acids are used by the de novo synthesis mechanisms to produce the saturated fatty acids of milk with 2 to 16 carbon atoms.

This synthesis, which takes place in the mammary epithelial cells, uses acetyl coA, a compound derived from C2 and/or C4 for these syntheses of C14: 0 and C16: 0.

These 2 fatty acids are then "shortened" (peroxisomal beta-oxidation) to produce short and medium-chain fatty acids of milk. These fatty acids can then optionally be desaturated into mono-unsaturated fatty acids under mammary desaturase activity.

4—Theoretical Model

The quantity of $CH_4$ produced per liter of milk therefore takes into account:
a) the animal's yearly milk production.

The more a dairy cow (for example) produces milk, the more the production of methane per liter of milk is decreased. Therefore, some authors propose the following equation:

Quantity of methane produced (kg per cow per year)=55.7+0.0098*(milk production, in kg per year and per animal).

b) ration composition, and in particular the quantity of available ALA in the rumen.

c) the ratio (C2+C4)/C3 in the rumen of these animals.

This VFA ratio is to be read as having a strong biological causal link with milk composition, in the form of the ratio between:

i) the sum of milk FAs with 16 or less than 16 carbon atoms, and ii) the sum of all the milk FAs.

The quantity of $CH_4$ produced per dairy female can therefore be calculated in relation to milk production (kg milk, per year, per animal) and to the FA composition of the milk from this animal.

It therefore appears that the person skilled in the art may have at hand a precious tool to evaluate the production of methane by dairy animals, in relation to their production level (easy to measure) and to the composition of the milk (easy to measure).

This indirect, but accurate, measurement of methane production can be used as a guide for the rationing systems of dairy ruminant animals, so as to reduce their contribution towards the greenhouse effect and to allow rapid measurement of the effects of these changes.

milk production (kg/animal/year);

the ratio between milk FAs having 16 carbon atoms or less as a % of total FAs.

Evidently, we could have chosen other FAs or other sums or ratios of FAs to illustrate the effects of de novo synthesis of saturated FAs in the udder, using the C2 produced in the rumen with $CH_4$ emission.

However, the sum of saturated FAs with 16 carbon atoms or less is particularly representative of this de novo synthesis from C2. Additionally, reading of the C16 fatty acids or of the sums of FAs with 12, 14, 16 carbon atoms, even the ratio between C16 and the sum of saturated FAs would also be relevant criteria.

This compiling of results was notably made from tests which firstly gave the FA profiles of milk and secondly gave measurements of methane produced per liter of milk, in tests using extruded flax seeds as ALA source and on cows having different production levels.

TABLE 1

Production of methane per litre of milk in relation to milk production per animal and to milk FA profile, over a given range of milk FA profile

| | MP | | | | | | | | | | |
|---|---|---|---|---|---|---|---|---|---|---|---|
| FA | 4 000 | 5 000 | 6 000 | 7 000 | 8 000 | 9 000 | 10 000 | 11 000 | 12 000 | 13 000 | 14 000 |
| 70 | 23.7 | 20.9 | 19.1 | 17.8 | 16.8 | 16.0 | 15.4 | 14.9 | 14.4 | 14.1 | 13.8 |
| 68 | 23.0 | 20.3 | 18.5 | 17.2 | 16.3 | 15.5 | 14.9 | 14.4 | 14.0 | 13.7 | 13.4 |
| 66 | 22.4 | 19.7 | 18.0 | 16.7 | 15.8 | 15.1 | 14.5 | 14.0 | 13.6 | 13.3 | 13.0 |
| 64 | 21.7 | 19.1 | 17.4 | 16.2 | 15.3 | 14.6 | 14.1 | 13.6 | 13.2 | 12.9 | 12.6 |
| 62 | 21.0 | 18.5 | 16.9 | 15.7 | 14.8 | 14.2 | 13.6 | 13.2 | 12.8 | 12.5 | 12.2 |
| 60 | 20.3 | 17.9 | 16.4 | 15.2 | 14.4 | 13.7 | 13.2 | 12.7 | 12.4 | 12.1 | 11.8 |
| 58 | 19.7 | 17.4 | 15.8 | 14.7 | 13.9 | 13.2 | 12.7 | 12.3 | 12.0 | 11.7 | 11.4 |
| 56 | 19.0 | 16.8 | 15.3 | 14.2 | 13.4 | 12.8 | 12.3 | 11.9 | 11.6 | 11.3 | 11.0 |
| 54 | 18.3 | 16.2 | 14.7 | 13.7 | 12.9 | 12.3 | 11.9 | 11.5 | 11.1 | 10.9 | 10.6 |
| 52 | 17.6 | 15.6 | 14.2 | 13.2 | 12.5 | 11.9 | 11.4 | 11.0 | 10.7 | 10.5 | 10.2 |
| 50 | 16.9 | 15.0 | 13.6 | 12.7 | 12.0 | 11.4 | 11.0 | 10.6 | 10.3 | 10.1 | 9.8 |
| 48 | 16.3 | 14.4 | 13.1 | 12.2 | 11.5 | 11.0 | 10.5 | 10.2 | 9.9 | 9.7 | 9.4 |
| 46 | 15.6 | 13.8 | 12.5 | 11.7 | 11.0 | 10.5 | 10.1 | 9.8 | 9.5 | 9.3 | 9.1 |
| 44 | 14.9 | 13.2 | 12.0 | 11.2 | 10.5 | 10.1 | 9.7 | 9.3 | 9.1 | 8.9 | 8.7 |
| 42 | 14.2 | 12.6 | 11.5 | 10.7 | 10.1 | 9.6 | 9.2 | 8.9 | 8.7 | 8.5 | 8.3 |

5—Test and Interpretation of Results

Numerous tests are available in the general bibliography which describe the effects of an intake of a food ALA source (most often in the form of flax) on the production of methane by cows, goats, and other female dairy ruminants.

Other tests are available which describe the effects of these same ALA sources, in the form of flax, on the fatty acid (FA) composition of milk.

Matching and synthesis of these results have been carried out to validate the theoretical model. These results are given in Table 1 below.

The focus here was to measure the production of $CH_4$ per liter of milk as a function of:

NB: This range of milk FA profile was deliberately limited to the range in which FAs with 16 carbon atoms or less account for 70 to 42% of the milk FAs. Not because the ensuing biological model or equation is limited to this range, but because beyond the limits of this range the composition of the milks produced can be considered firstly to be nutritionally doubtful and secondly incompatible with the above-defined means used to obtain these milks.

In this table: MP (horizontally)=milk production (kg/animal/year) and FA=[FA<C16/Total FAs], as a %.

We have therefore drawn up a predictive table for emitted $CH_4$ values on the basis of milk production data and the FA profiles of these milks so produced:

TABLE 2

| | MP | | | | | | | | | | |
|---|---|---|---|---|---|---|---|---|---|---|---|
| FA | 4 000 | 5 000 | 6 000 | 7 000 | 8 000 | 9 000 | 10 000 | 11 000 | 12 000 | 13 000 | 14 000 |
| 70 | 23.0 | 20.9 | 19.3 | 18.1 | 17.1 | 16.2 | 15.5 | 14.9 | 14.4 | 13.9 | 13.5 |
| 68 | 22.3 | 20.3 | 18.8 | 17.6 | 16.6 | 15.8 | 15.1 | 14.5 | 14.0 | 13.5 | 13.1 |

TABLE 2-continued

| | | | | | MP | | | | | |
|---|---|---|---|---|---|---|---|---|---|---|
| FA | 4 000 | 5 000 | 6 000 | 7 000 | 8 000 | 9 000 | 10 000 | 11 000 | 12 000 | 13 000 | 14 000 |
| 66 | 21.7 | 19.7 | 18.2 | 17.1 | 16.1 | 15.3 | 14.6 | 14.1 | 13.5 | 13.1 | 12.7 |
| 64 | 21.0 | 19.1 | 17.7 | 16.5 | 15.6 | 14.9 | 14.2 | 13.6 | 13.1 | 12.7 | 12.3 |
| 62 | 20.3 | 18.5 | 17.1 | 16.0 | 15.1 | 14.4 | 13.8 | 13.2 | 12.7 | 12.3 | 11.9 |
| 60 | 19.7 | 17.9 | 16.6 | 15.5 | 14.6 | 13.9 | 13.3 | 12.8 | 12.3 | 11.9 | 11.5 |
| 58 | 19.0 | 17.3 | 16.0 | 15.0 | 14.2 | 13.5 | 12.9 | 12.4 | 11.9 | 11.5 | 11.1 |
| 56 | 18.4 | 16.7 | 15.5 | 14.5 | 13.7 | 13.0 | 12.4 | 11.9 | 11.5 | 11.1 | 10.8 |
| 54 | 17.7 | 16.1 | 14.9 | 14.0 | 13.2 | 12.5 | 12.0 | 11.5 | 11.1 | 10.7 | 10.4 |
| 52 | 17.1 | 15.5 | 14.4 | 13.4 | 12.7 | 12.1 | 11.5 | 11.1 | 10.7 | 10.3 | 10.0 |
| 50 | 16.4 | 14.9 | 13.8 | 12.9 | 12.2 | 11.6 | 11.1 | 10.7 | 10.3 | 9.9 | 9.6 |
| 48 | 15.8 | 14.3 | 13.2 | 12.4 | 11.7 | 11.1 | 10.6 | 10.2 | 9.9 | 9.5 | 9.2 |
| 46 | 15.1 | 13.7 | 12.7 | 11.9 | 11.2 | 10.7 | 10.2 | 9.8 | 9.4 | 9.1 | 8.8 |
| 44 | 14.4 | 13.1 | 12.1 | 11.4 | 10.7 | 10.2 | 9.8 | 9.4 | 9.0 | 8.7 | 8.5 |
| 42 | 13.8 | 12.5 | 11.6 | 10.9 | 10.3 | 9.7 | 9.3 | 8.9 | 8.6 | 8.3 | 8.1 |

6—Validation of this Model

We have the results of several tests which accurately measured:
  the quantity of ALA (available in the rumen) in the rations of dairy cows;
  the effects of this ALA on the ratio (C2+C4)/C3;
  the effects of these rations on the milk FA profile;
  and finally tests which compared the production of $CH_4$ per liter of milk with different ALA contents in the rations.

The table below compares the measured values with the values "predicted" from the above-mentioned tables.

TABLE 3

| Tests | 1 | 2 | 3 | 4 | 5 | 6 |
|---|---|---|---|---|---|---|
| Milk production | 6 000 | 6 000 | 7 000 | 7 000 | 7 000 | 6 000 |
| FA >= C16 | 61 | 42 | 66 | 64 | 56 | 42 |
| $CH_4$ in g/l milk "Prediction" in g/l | 16.8 | 11.8 | 17.2 | 16.2 | 13.8 | 10.9 |
| As per Table 1 | 16.4 | 11.5 | 17.2 | 16.2 | 14.2 | 11.5 |
| As per Table 2 | 16.4 | 11.5 | 17.2 | 15.7 | 14.2 | 11.5 |

The present applicant has inferred from these tests that the quantity of methane can be defined by the following equation:

$$\text{Quantity } CH_4 = (FA<C16/\text{Total FAs}) * a * (\text{milk production})^b$$

in which:
  quantity $CH_4$ (in g/liter of milk)=quantity of methane produced;
  FA<C16=quantity of fatty acids with 16 carbon atoms or less;
  Total FAs=total quantity of fatty acids;
  milk production=quantity of milk produced in kg per animal per year
  a and b=numerical parameters in which a lies between 10 and 13, and b lies between −0.40 and −0.45.

Preferably, parameters a and b are 11.368 and −0.4274 respectively.

The invention claimed is:

1. A method for reducing or controlling the quantity of methane produced by a dairy ruminant comprising:
  A. determining the quantity of methane produced by the dairy ruminant comprising:
    determining in the milk comprising fatty acids produced by the ruminant the ratio between the amount of fatty acids with 16 carbon atoms or less in the milk and the total amount of fatty acids in the milk;
    using the ratio to calculate the quantity of methane in g/liter of milk produced by the ruminant using the equation:

$$\text{Quantity } CH_4 = (FA<C16/\text{Total FAs}) * a * (\text{milk production})^b,$$

wherein,
    FA<C16=the amount of fatty acids with 16 carbon atoms or less;
    Total FAs=total amount of fatty acids;
    milk production=kg of milk per animal per year;
    a is between 10 and 13; and
    b is between −0.40 and −0.45; and
  B. in response to the quantity of methane calculated, reducing or controlling the quantity of methane produced by the dairy ruminant by providing the ruminant with a food ration which meets at least one of the following criteria:
    (a) the food ration excludes all fat of animal origin;
    (b) the food ration limits the exogenous intake of vegetable oil containing more than 30% saturated fatty acids in the natural state, saponified, or hydrogenated to no more than 15 grams per 100 kg live weight of each animal; and
    (c) the food ration contains at least one lipid source in which the amount of omega-3-alpha-linolenic acid is at least 30% of the total fatty acids.

2. The method of claim 1, wherein a is 11.368 and b is −0.4274.

3. The method of claim 1, wherein the ration is given which accumulatively meets the three criteria.

4. The method of claim 1, wherein the omega-3-alpha-linolenic acid is used in the form selected from the group consisting of grazed fodder, conserved forage, oilseeds, oilcakes of oilseeds, flax and combinations thereof.

5. The method of claim 4, wherein the grazed fodder or conserved forage is selected from the group consisting of wilted grass, silage, wrapped round bale, dehydrated grazed fodder, dehydrated conserved forage, and combinations thereof.

6. The method of claim 4, wherein the oilseeds or oilcakes are in the form selected from the group consisting of the natural state, raw, cooked, and combinations thereof.

* * * * *